United States Patent [19]

Illi

[11] Patent Number: 5,129,904

[45] Date of Patent: Jul. 14, 1992

[54] OSTEOSYNTHETIC IMPLANT

[76] Inventor: Oscar E. Illi, Geeringstrasse 42, CH-8049 Zürich, Switzerland

[21] Appl. No.: 357,646

[22] Filed: May 24, 1989

Related U.S. Application Data

[63] Continuation of Ser. No. 76,614, Jul. 23, 1987, abandoned.

[30] Foreign Application Priority Data

Aug. 5, 1986 [CH] Switzerland .................. 03152/86

[51] Int. Cl.⁵ .......................... A61F 5/28; A61F 2/28
[52] U.S. Cl. .......................................... 606/72; 623/16
[58] Field of Search ................... 623/11, 12, 16, 18; 606/60, 65, 69, 72, 73, 74

[56] References Cited

U.S. PATENT DOCUMENTS

| 3,739,773 | 6/1973 | Schmitt et al. | 623/16 |
|---|---|---|---|
| 4,209,859 | 7/1980 | Hoffman | 623/16 |
| 4,329,743 | 5/1982 | Alexander et al. | 623/18 |
| 4,484,570 | 12/1984 | Sutter et al. | 623/16 |
| 4,512,038 | 4/1985 | Alexander et al. | 623/16 |
| 4,539,981 | 9/1985 | Tunc | 623/16 |
| 4,711,232 | 12/1987 | Fischer et al. | 128/924 F |
| 4,716,893 | 1/1988 | Fischer et al. | 128/924 F |

FOREIGN PATENT DOCUMENTS

| 191081 | 9/1956 | Austria | 128/924 F |
|---|---|---|---|
| 0011528 | 5/1980 | European Pat. Off. . | |
| 0159502 | 10/1985 | European Pat. Off. . | |
| 3509417 | 9/1986 | Fed. Rep. of Germany . | |
| 1205743 | 9/1970 | United Kingdom | 623/1 |

Primary Examiner—David Isabella
Attorney, Agent, or Firm—Speckman & Pauley

[57] ABSTRACT

Two bone fragments may be connected by means of an osteosynthetic implant including connecting device and connecting bands comprising reabsorbable, biocompatible material, such as, for example, polygluconate or polylactate, the bands preferably in woven or knit form, and connected to the bone fragments by means of connecting elements. Different types of connecting elements are suitable for use with different types of bone fragments to be connected, and may comprise either tamping liners with tamping counterpieces or hollow screws. The connecting elements have an internal hollow bore, and may be implanted with a special tool to prevent any breakage of the connecting elements. The osteosynthetic implant comprising reabsorbable material is particularly suitable for osteosynthesis in children, since growth disturbances are eliminated.

6 Claims, 2 Drawing Sheets

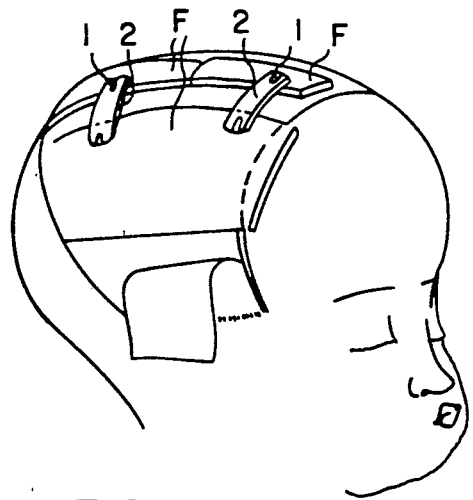
FIG. 1
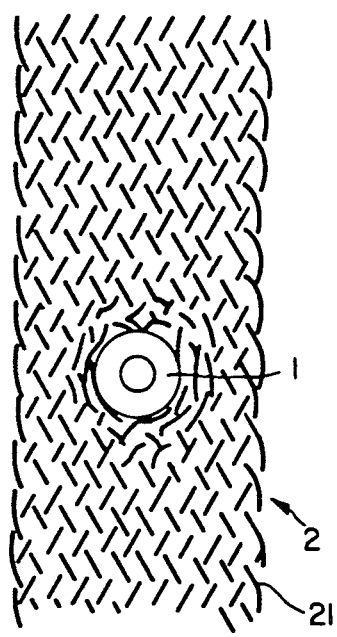
FIG. 2
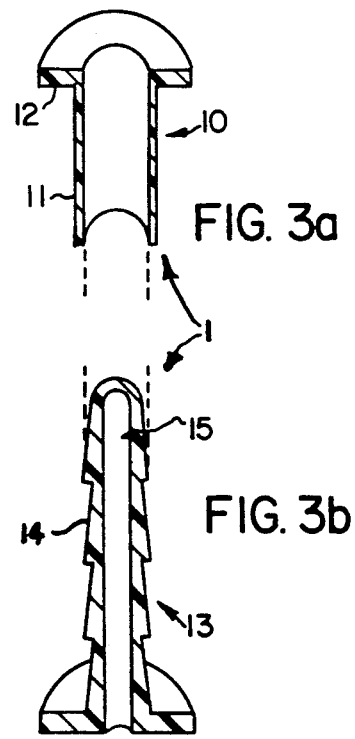
FIG. 3a
FIG. 3b
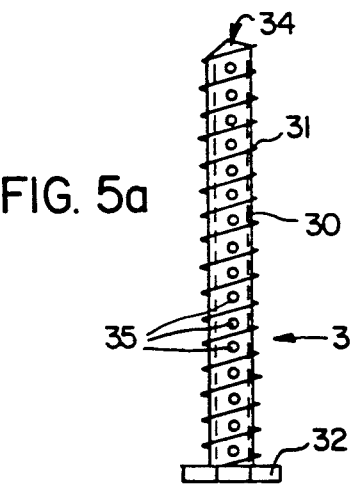
FIG. 5a
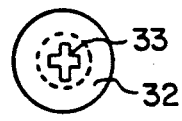
FIG. 5b
FIG. 5c

OSTEOSYNTHETIC IMPLANT

Cross Reference to Related Application

This is a continuation application of co-pending application Ser. No. 07/076,614, filed July 23, 1987 now abandoned.

BACKGROUND OF THE INVENTION

1. Field of the Invention

The present invention relates to an osteosynthetic implant for the fixation and/or support of flat and tubular bone fragments, particularly in children.

2. Description of the Prior Art

Osteosynthetic implantation is currently practiced primarily in adults. Only in a very limited number of cases, such as, for example, in multiple fractures, is osteosynthetic implantation practiced with children during their growth years. The use of synthetic implants in children may result, it is known, in growth disturbances which require corresponding surgical corrections. Preliminary experiments with osteosynthetic connecting elements were performed, although not specifically with reference to pediatric surgery, using screws made from reabsorbable material. The results of these experiments were not encouraging, particularly as regards implantation of the osteosynthetic connecting elements. The range of application was limited, but the screws generally did not withstand stresses produced during the process of implantation. The screw heads generally broke because the reabsorbable material had insufficient strength. Also, the problem of fixation was not solved for those cases in which the individual bone fragments had to be supported by additional elements such as plates or cerclage units.

Work proceeded from considerations and experiences gained from osteosynthetic implantation in adults. In the use of metal implants, a level of microstability must be attained, that is to say, a level of stability which permits only the smallest movements between the fragments. Microstable connections permit stresses of approximately 60-80 kp over the area of the fracture, without perceptible movements being noted.

The considerable elasticity of bones of children and adolescents in their growth years permits, however, a level of macrostability. Macrostable connections, subjected to a stress of 10-20 kp over the area of the fracture, still permit slight, perceptible movements. The fracture is thereby stable as to support and movement. A microstable osteosynthetic implantation such as is achievable, for example, in adult surgery, is not intended for children and adolescents.

This knowledge is consciously utilized by the inventor to provide a new osteosynthetic implant which is suitable for use in pediatric surgery.

SUMMARY OF THE INVENTION

It is an object of the present invention to provide a synthetic implant for pediatric surgery which provides osteosynthetic contacts causing no growth disturbances, or only very slight levels of growth disturbances.

The osteosynthetic implant of the present invention comprises a band of reabsorbable material which is attachable to bone fragments by means of connecting elements of reabsorbable material penetrating the band and the bone fragments. The use of connecting elements comprising reabsorbable material with the bands, which function like tension belts, enables osteosynthetic implantation even in children during their growth years without causing growth disturbances, and achieves the necessary macrostability.

In fractures of hollow cylindrical bones, hollow screws having a head, a central bore with a regular cross-sectional configuration, such as a cylindrical bore with extended portions directed radially outwardly in a cruciform fashion, and an axial penetrating aperture provided at the tip of the screw are preferred. Such screws require the use of a special tool for implantation, by means of which the distribution of force during insertion of the screws is even over approximately the entire length of the screw, so that the screw does not break during insertion.

The extended portions of the cylindrical bore may be constructed as channel grooves to avoid any outwardly directed force to prevent the screw from breaking.

The penetration of the screws and the reabsorption of the reabsorbable material of the screws and bands is improved when the hollow screws are provided with radially penetrating holes.

The tool which is disclosed for use during osteosynthetic implantation using the hollow screws described above comprises a screwdriver having an external contour corresponding to the cross-sectional configuration of the internal bore of the screw, and an axial centering pin. The centering pin serves to guide the screw in an aligning manner with respect to the bore hole in the bone.

In order, on the one hand, to penetrate the bands, and, on the other hand, to center the screw in the bore of the bone fragment, it is preferred that the centering pin is supported in an axially displaceable manner against spring pressure in the screwdriver.

BRIEF DESCRIPTION OF THE DRAWINGS

The invention is described in greater detail and illustrated in the following drawings, in which:

FIG. 1 shows an example of craniofacial application of the osteosynthetic implant of the present invention;

FIG. 2 shows a top view of a band with a connecting element comprising reabsorbable material;

FIGS. 3a and 3b show a perspective view of a tamping liner and a tamping counterpiece in cross section;

FIG. 5a shows a side view of the hollow screw used in the osteosynthetic implant shown in FIG. 4;

FIG. 5b shows an end view of the head of the hollow screw shown in FIG. 5a;

FIG. 5c shows an end view of the tip of the hollow screw shown in FIG. 5a;

FIG. 6 shows a perspective view of a screwdriver for use in implanting the hollow screw shown in FIG. 5a;

DESCRIPTION OF PREFERRED EMBODIMENTS

Figure 4:
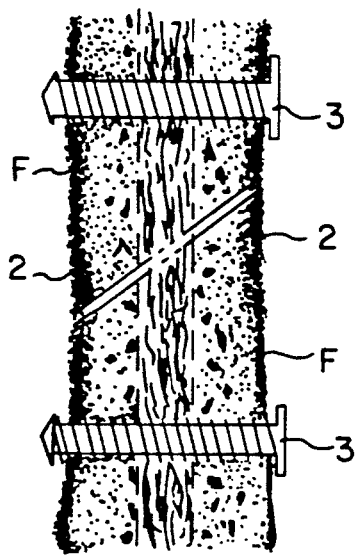
FIG. 4 shows a cross-sectional view illustrating the use of the osteosynthetic implant with hollow screws for a hollow cylindrical bone fracture.

The osteosynthetic implant in accordance with the present invention utilizes connecting elements and bands, the bands serving as tension belts which evenly transfer forces from one bone fragment to the other to fix both fragments in place. The connecting elements penetrate the band or bands and the corresponding bone fragments. The bone fragments are designated by reference letter (F) in the figures. Connecting elements (1), which, in practice, are only a few millimeters in diameter, are shown in the diagram as points. The bands are designated by reference numeral (2). The distance between the bone fragments is, for the sake of clarity, depicted on a larger scale than life-size.

An enlarged view of one embodiment of the osteosynthetic implant is shown in FIG. 2. Band (2) is knit or woven from filaments of reabsorbable biocompatible materials. The mesh width, the filament distance, and the shape are selected so that the tissue or weave is easily penetrated by the connecting elements. It is essential that the elastic deformation of the band in the longitudinal direction be relatively slight. Longitudinal elastic deformation is influenced by the corresponding filament shape and weave. As FIG. 2 shows, filaments (21) are preferably only displaced in the area where connecting elements penetrate the band (2).

Depending upon the type of bone fragments to be connected, different connecting elements may be used. Connecting elements may be fabricated from known materials, such as, for example, polygluconate, polylactate, and the like, which are biodegradable and biocompatible.

In FIGS. 3a and 3b, connecting elements suitable for connecting flat bone fragments are shown in a perspective, cross-sectional view. A tamping liner is designated by reference numeral (10), comprising tubular part (11) with an annular collar unit (12) at one end. According to a preferred embodiment, the wall thickness of annular collar unit (12) may be, for example, about 0.5 mm, with a total length of approximately 2 mm. The diameter of collar unit (12) may be approximately 5 mm, while the internal diameter of the tubular part (11) may be approximately 2 mm. Tamping counterpiece (13) is graduated in diameter and is formed like a peg or tamping unit. External serrations (14) ensure a good press fit during implantation and prevent tamping liner (10) or counterpiece (13) from breaking during assembly. Central cylindrical blind hole (15) provides a mounting support for the counterpiece on a surgical instrument, for example, a specialized pair of parallel tongs, which facilitates implantation. The length of the tamping counterpiece is preferably greater than the length of tamping liner (10), because the liner should generally be shorter than the thickness of the flat bone. It is, however, also possible to work with screws and nuts, wherever this is advantageous due to considerations of accessibility.

While in the case of flat bone connections, the bands used for joining bone fragments often are only applied on one side of the bone, it is both possible and desirable in the case of tubular bone fragments to apply bands (2) to two opposing sides of the bone. Connecting elements penetrate both bands and have an effect comparable to that of a tension belt.

For a connection of tubular bone fragments, hollow screws (3) are preferably used as connecting elements. A suitable hollow screw (3), is shown in FIGS. 5a-c. Hollow screw (3) comprises shaft (30) provided on its entire length with external screw threading (31) with relatively great thread course distances. Head (32) of the screw is preferably flat, and forms a collar. The hollow screw is penetrated by a central bore (33) preferably over its entire length. This may be formed in various ways. It is important in a preferred embodiment that the central bore has extended portions which are directed radially outwardly. In the embodiment shown in FIGS. 5b and 5c, the central bore is generally circular with four radial grooves spaced equidistantly from one another in a cruciform arrangement. The end of the screw is penetrated by an axial passage hole (34), the purpose of which will be further described below. Several radial bores (35), which penetrate to central internal bore (33) serve to promote tissue-like intermingling and facilitate the biological decomposition of the screw.

Figure 6:
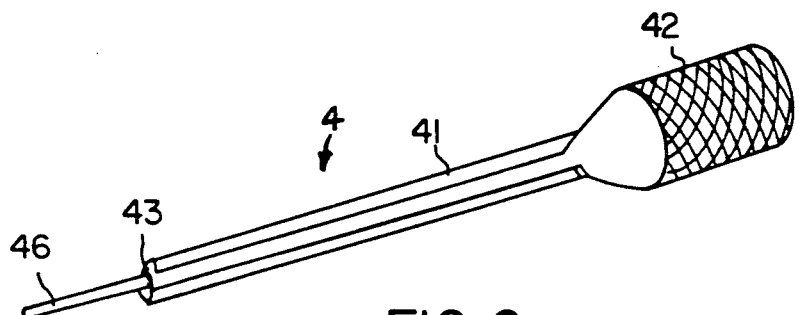
Figure 7:
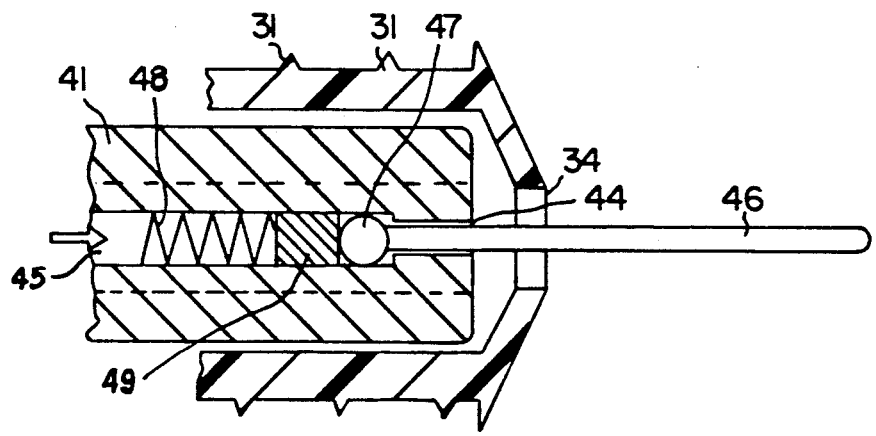
FIG. 7 shows an enlarged cross-sectional view of the terminal end of the screwdriver in the shaft of a hollow screw.

To implant the hollow screw, a special screwdriver tool is necessary. This tool resembles an Imbuss key wrench having a cross-sectional configuration corresponding to the configuration of central bore (33) of the screw. Tool (4) is shown in its entirety in a perspective view and shown partially and in an enlarged cross-sectional view in FIGS. 6 and 7, respectively. Tool (4) comprises hollow shaft (41), which is cruciform in cross-sectional configuration corresponding to central bore (33) of the screw, and has an enlarged end which serves as handle (42). Handle (42) may be attached to the shaft by screwing. At the tip of the shaft, a bore (44), is provided, through which a centering tip (46) projects, the centering tip being axially adjustable in the internal bore (45) of shaft (41). Centering tip (46) is enlarged at one end to form a guide piece (47), which is retained in internal bore (45). Helical compression spring (48) with pressure plates (49) displaces the centering tip to its initial end position. Compression spring (48) has its catching stud on handle (42), which may be removed by screwing.

Centering tip (46) serves, during the osteosynthetic implantation, as a guide means. Screw (3) is mounted on screwdriver tool (4), with centering tip (46) projecting through screw (3) and through axial passage hole (34) at the tip of screw (3).

It is possible, by means of centering tip (46), to penetrate band (2) and the already prepared bore in the bone fragment, and thus prepare the way for the screw implant. On the opposing side of the band, the filaments of the band (2) are penetrated and the bore provided in the bone fragment is also penetrated by the centering tip (46). Since the tip is axially adjustable by means of the spring, the danger of centering tip (46) causing injuries may be avoided.

The cruciform external contour of screwdriver tool shaft (41), which precisely corresponds to the cross-sectional configuration of central internal bore (33) of screw (3), conveys, even with a relatively high level of torque, very slight surface pressure to screw (3), and avoids radial forces, which may cause bursting and destruction of the screw. The force therefore need no longer be transferred to the shaft of the screw (30) through the head of the screw (32). The danger of a disturbance and material failure is thereby considerably reduced. If such a breakage should nonetheless occur, then the contact between the remaining parts and the screwdriver is still preserved, and the parts can be screwed out again later.

Figure 8:
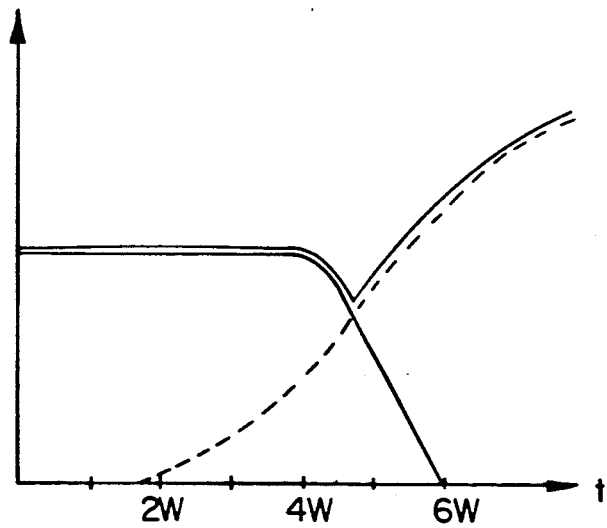
FIG. 8 shows a graphical representation of the strength of the connection between the bone fragments in relation to the healing time.

Finally, the sequence of the healing process using the new osteosynthetic implant will be briefly described. In this regard, reference is made to the graphic representation shown in FIG. 8. Time is marked on the abscissa of the coordinate system, while the ordinate represents the strength of the connection between the bone fragments connected. The curves merely represent qualitative and not quantitative relationships. Initiation of the operative contact is considered to be at time point "0". The strength of the connection initially corresponds to the strength of the implant used. This is represented as a lightly drawn unbroken line. The biological decomposition of the reabsorbable material of the osteosynthetic implant, which causes a decrease in its strength, begins after about four weeks. However, the connective tissue-like intergrowth and penetration of the implant begins after only two weeks. The strength during the intergrowth period is depicted by dotted lines. Ossification begins at about the fourth to the sixth week, approximately, when the strength of the intergrowth then increases over the strength of the implant connection. The overall strength of the connection does not correspond to the summation of both strength values, but is rather represented by the curve which is shown as a thick, unbroken line.

During the relatively short time which elapses until biodegradation of the reabsorbable material occurs, the osteosynthetic implant does not give rise to growth disturbances.

A second surgical procedure for removing the implant is eliminated by the practice of the present invention. Through this, particularly in the case of the infantile skeletal structures, an additional detriment to growth caused by the operation and the exposure of the bone is prevented.

Overall, the length of incapacitation, as well as the total costs of the clinical treatment are thus considerably reduced.

In FIG. 2, band (2) is depicted in a woven form. The relatively loose weave facilitates penetration of the connecting elements through band (2). To prevent the bands from ripping during penetration, it is important that the warp threads be heat molded with the longitudinal filaments.

I claim:

1. An osteosynthetic implant for the fixation and support of tubular bone fragments comprising: at least one connecting band (2) attachable to join said bone fragments by means of at least two hollow screws (3), each said screw having a flat head (32), external threading (31) for an entire length of a shaft of each said screw, a central bore (33) extending through said flat head (32) and along said entire length said shaft of each said screw, said central bore (33) having a cross-sectional configuration with radially inwardly directed extensions substantially along the length of the bore mateable with elongated tool means having a cross section corresponding to said cross-sectional configuration of said central bore (33) for applying an evenly distributed force to said screw for torquing said screw, and each said screw having an axial through hole at a tip of each said screw; said screws penetrating said connecting band (2) and said bone fragments, said connecting band (2) and said screws (3) being of a reabsorbable biocompatible material.

2. An osteosynthetic implant in accordance with claim 1, wherein said connecting band (2) has woven filaments comprising warp filaments heat sealed with longitudinal filaments at uniform distances.

3. An osteosynthetic implant in accordance with claim 1, wherein said connecting band (2) has woven filaments (21) which cross one another at an angle of approximately 60°.

4. An osteosynthetic implant in accordance with claim 1, wherein said connecting band (2) comprises knit filaments.

5. An osteosynthetic implant in accordance with claim 1, wherein said radially directed extensions of said central bore (33) further comprise equidistantly spaced hollow grooves.

6. An osteosynthetic implant in accordance with claim 1, wherein said hollow screws (3) further comprise a plurality of radial bores (35) which extend to said central bore (33).

* * * * *